United States Patent
Kripp et al.

(10) Patent No.: US 7,078,025 B2
(45) Date of Patent: Jul. 18, 2006

(54) TWO COMPONENT AGENT WITH A TIME DEPENDANT PH AND METHOD OF TREATING HAIR WITH SAID AGENT

(75) Inventors: Thomas Kripp, Fraenkisch-Crumback (DE); Beate Grasser, Hattersheim (DE); Achim Koschik, Darmstadt (DE)

(73) Assignee: Wella AG, Damstadt (DE)

( * ) Notice: Subject to any disclaimer, the term of this patent is extended or adjusted under 35 U.S.C. 154(b) by 488 days.

(21) Appl. No.: 10/224,187

(22) Filed: Aug. 20, 2002

(65) Prior Publication Data

US 2003/0075197 A1    Apr. 24, 2003

(30) Foreign Application Priority Data

Sep. 20, 2001 (DE) ............................... 101 46 350

(51) Int. Cl.
*A61K 8/00* (2006.01)

(52) U.S. Cl. ...................................... 424/70.2; 132/203

(58) Field of Classification Search ........ 132/202–209; 424/400, 401, 70.1, 70.2, 70.4, 70.5, 70.51
See application file for complete search history.

(56) References Cited

U.S. PATENT DOCUMENTS 5,935,589 A * 8/1999 Mukherjee et al. ......... 424/401
6,096,348 A * 8/2000 Miner et al. ................ 424/616

FOREIGN PATENT DOCUMENTS

| DE | 1 089 124 | 9/1960 |
| DE | 23 49 050 | 4/1975 |
| DE | 199 02 246 A1 | 9/1999 |
| DE | 198 60 239 C2 | 11/2000 |

* cited by examiner

*Primary Examiner*—Todd E. Manahan
(74) *Attorney, Agent, or Firm*—Michael J. Striker

(57) ABSTRACT

The two-component hair treatment product consists of one component (A) and another component (B). Component (A) contains an acid and component (B) contains a base. Less than 3 g of the base and/or acid are soluble in 100 ml of water at 20° C. The acid is preferably a dicarboxylic acid, such as sebacic, dodecanoic dicarboxylic acid or tetradecanoic dicarboxylic acid. The base is preferably ammonia, an alkyl amine or an alkylol amine. Prior to use in a method of permanent hair shaping or hair care, the components are mixed with each other to form a ready-to-apply mixture having an automatically continuously or gradually changing pH that changes within from one to 60 minutes so that damage to the hair due to high pH is avoided. For permanent shaping of hair the initial pH of 8 to 13 falls from about 1 to 4 pH units within from 10 to 30 minutes after mixing the components.

20 Claims, 1 Drawing Sheet

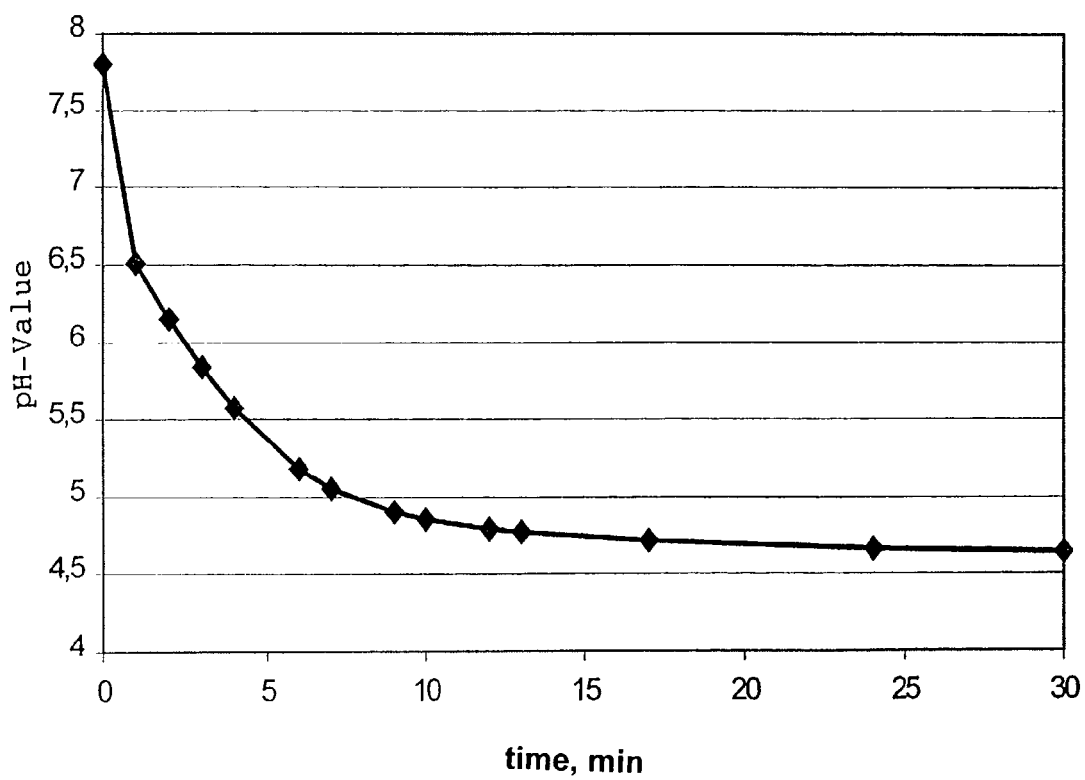

TWO COMPONENT AGENT WITH A TIME DEPENDANT PH AND METHOD OF TREATING HAIR WITH SAID AGENT

BACKGROUND OF THE INVENTION

The subject matter of the present invention comprises a two-component agent or product with a pH value that automatically changes within a time period of from 1 to 60 minutes in a time delayed fashion after mixing the two components. The two-component agent comprises one component (A) containing at least one acid and another component (B) containing at least one base. The acid and/or the base have reduced water solubility. The subject matter of the invention also includes a method of treating hair, especially a method of caring for hair or for permanent shaping of the hair.

Although most chemical, technical, food technology and cosmetic products have the same pH value from the start to finish during their usage, there have been many attempts to provide systems for certain special applications, which change their pH after application.

Different reasons can require these special applications, for example

A substance has a pH value, at which it is most effective but is only storage-stable to a limited extent;

A pH-dependent activity, which should be controlled in its time dependence;

Two pH-dependent activities, which have respective different optimum pH values following each other, in spite of only one-time application;

A reaction delay should be provided, in order to allow a previous diffusion; and A color change should indicate the end of activity.

A method for permanent shaping is described in DE 1089124 A1, in which ammonia is released from urea with the help of urease and provides an increase in the pH during the acting time.

A composition and method are known from DE 23 49 050 A, in which waving effectiveness is continuously reduced by lowering the pH. Immediately prior to application alkali cleavable organic compounds with ester or halo groups in the molecule that produce acid when cleaved are added to the permanent shaping agent. Because of that addition the concentration of alkali during the acting time generally decreases and is in the desired range. For example, acetic acid ethyl ester and triacetin are generally suitable as the esters. An acceleration of the cleavage rate of the compounds containing the ester groups can be achieved by addition of the lipase, Pancreatin.

A system is known from DE-PS 198 60 239 C2, in which the pH behavior of the permanent wave solution changes with time because of enzymatic cleavage of esters, especially e.g. triglycerides, and simultaneous counter buffering of the pH behavior, in order to reduce the initial waving effectiveness after a brief time and also to prevent exceeding a pH of 7.0.

A system is known from DE 199 02 246 A1, in which pH is lowered by non-enzymatic hydrolysis of a sufficiently unstable lactone. The speed and end point of this non-enzymatic hydrolysis depend on the type and concentration of the concerned educt within the scope of the conditions (temperature, initial pH, etc).

Each of these systems has a serious disadvantage: If the rate of pH change is produced by enzyme-catalyzed reactions, it is extremely difficult to set (and above all to maintain) a definite course of the pH or pH-time variation. The enzymatic activity and thus the kinetics of the pH behavior changes with the storage conditions. Thus a three-component system is usually required for the foregoing reason: One component for the hair product, one component (strictly water-free) for the hydrolyzed ingredient and one for the enzyme. Additionally during application an excessive effort is necessary to mix the three components completely and homogeneously. Also performing the mixing sufficiently rapidly is troublesome and not without problem.

The spontaneous hydrolysis of the lactones disclosed in DE 199 02 246 A1 avoids the problem of enzyme catalysis; generally only a limited number of suitable compounds exist. The hydrolysis conditions for the concerned material are definitely dependent on the nature of the substance and the formulation of the components can hardly effect it, so that no noteworthy possibility exists to adjust this sort of system to different conditions or starting materials.

It is common to all the methods described here that the "normal" product mass must be mixed with "non-normal" components (water-free suspensions, crystalline or powdery substances). The expression "normal" here relates to the chemical composition and pleasing character, i.e. the color, smell, flow properties, viscosity, haptic properties.

SUMMARY OF THE INVENTION

It is an object of the present invention to develop systems, which provide a pH that varies with time and has the following properties:

It only contains components with "normal" pleasing characteristics;

It contains no hydrolytically released substances;

It contains no enzymatically released substances;

It has high storage stability for all components;

It requires a maximum of two separate components;

It is adjustable regarding the position of the varying pH range;

It is adjustable regarding the size of the varying pH range;

It is adjustable in regard to the direction of the pH change; and

It is adjustable regarding the rate of the pH change.

According to the invention a two-component agent or product is provided which produces a pH that automatically gradually or continuously changes with time during a one minute to 60 minute time period after mixing the components. One component contains at least one acid and another component contains at least one base. Less than 3 g of the at least one acid and/or the at least one base can be dissolved in 100 ml of water at 20° C.

With the two-component agent and/or method for hair treatment according to the invention an acid is brought into contact with a base. The acids and/or bases suitable for this purpose are—in contrast to their salts—only weakly soluble in water. Preferably only the acid is slightly soluble. The salt formation (e.g. the reaction at the start in mixture with excess base) occurs chiefly with a small fraction of acid, which can be determined according to the equilibrium constant for the solution. The salt formation (and thus the neutralization of the base) is delayed during the equilibration because of the reduced solubility of the acid. For this no suspension is used, but preferably a co-emulsifier comprising a lipophilic compound (which is preferably a fatty alcohol, a triglyceride, a paraffin oil or a wax) and the concerned acid.

Reaction Scheme:

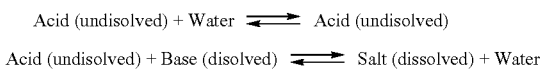

The acids suitable for the invention should preferably have the following properties:
Reduced water solubility (preferably under 2%):
Relatively high acidity;
Lower melting point (preferably under 150° C.);
No noteworthy odor;
No noteworthy effect on the standard formulation.

It is especially preferably when from 0.01 to 1.0 g of the at least one acid and/or at least one base is or are soluble at 20° C. in 100 ml of water. It is most preferred when from 0.05 to 0.5 g of the at least one acid and/or at least one base is or are soluble at 20° C. in 100 ml of water.

In a preferred embodiment of the two component agent the first component (A) includes an acid which is only soluble in amounts less than 3 g in 100 ml of water at 20° C. as the acid ingredient and the second component (B) contains at least one inorganic base or organic base having from 1 to 40 carbon atoms.

The aliphatic monocarboxylic acids, which are acceptable regarding odor, have a chain length, which makes them too little acidic, whereas the corresponding sulfonic acids with a great chain length are too water-soluble. Surprisingly hydrophobic dicarboxylic acids with 6 to 22 carbon atoms, preferably with 8 to 16 carbon atoms, have proven to be ideal. These latter acids are especially preferred. Hydrophobic dicarboxylic acids with 6 to 22 carbon atoms are odorless and sufficiently acidic and are available to a large extent with different chain lengths (hydrophobicity). The dicarboxylic acids with $C_8$-(octanedioic acid) to $C_{22}$-(docosanedicarboxylic acid) dicarboxylic acids. They produce a time delayed pH drop to the desired extent on contact with different bases under different conditions. Sebacic acid, dodecanoic dicarboxylic acid and tetradecanoic dicarboxylic acid are especially preferred acids.

All bases, especially inorganic bases, such as LiOH, NaOH, KOH, $Ca(OH)_2$, ammonia and hydrazine, are suitable. Also organic bases having 1 to 30 carbon atoms are especially suitable. For example the primary, secondary and tertiary alkyl amines and alkyl diamines and alkylol amines with 2 to 20 carbon atoms in their alkyl groups are suitable organic bases.

Both the acids and also bases can be present in a concentration of 0.01 to 10 percent by weight based on a total amount of the mixture of components (A) and (B).

A preferred embodiment of the two-component agent or product according to the invention is characterized by a time varying pH, wherein, starting from an initial pH of the mixture, the final pH of the mixture is reached after a time interval of 2 to 100 minutes, after mixing the components. It is especially preferred when the initial pH is higher than the final pH and the time interval for reaching the final pH is from 4 to 30 minutes.

In a preferred embodiment of the invention the pH behavior is made visible to an observer by addition of one or more indicator substances, which change color at different pH values, to one of the components (A) or (B). According the pH behavior and the type of indicator a color can appear, disappear or change.

An increase of delay time with simultaneous reduction of the achievable end point pH could surprisingly be achieved in other embodiments by working a slight water-soluble base, such as myristyl amine, into the alkaline compound (B). It can be adjusted, as needed, by partial neutralization with a suitable organic or inorganic acid to the desired initial pH value.

In additional embodiments of the invention a fatty phase comprising at least one fatty amine is included in the basic component (B), which is partially neutralized by means of the hydrophobic dicarboxylic acids. A typical pH behavior occurring when equal volumes of both components are mixed is shown in the appended graphical illustration.

The time duration, intensity, range selection and direction of the pH change can be adjusted by a combination and selection of the at least one acid and at least one base, their respective concentrations and their concentration ratios and in wide ranges.

The methods described here for providing a time varying pH gradient by retardation of salt formation can be used for products based on dispersions of all sorts, such as O/W-emulsions and W/O-emulsions, microemulsions, suspensions, liquid crystal phases, gels, foams and aerosols. These products are used for cleaning, care, sealing, dyeing or other treatments of surfaces.

The two-component agent or product is especially suitable for packaging as a cosmetic agent, preferably for skin, teeth and hair cosmetics. The two-component agent according to the invention is especially preferred in the form of a hair cosmetic product, for example a hair care composition, a shampoo, a styling gel, a hair fixing agent, a permanent wave composition, a fixing composition, a hair bleach, a hair dye or hair tinting agent. The two-component agent according to the invention preferably contains from 1 to 20 percent by weight of a lipophilic compound. This lipophilic compound is selected from the group consisting of fatty alcohols, triglycerides, paraffin oils or waxes.

The subject matter of invention also comprises methods for treating hair, in which the component (A) is mixed with the component (B) of the two-component agent immediately prior to application, the hair is treated with the resulting ready-to-apply mixture and, after an acting time, the hair is rinsed to remove the remaining mixture. The two-component agent used in the method is the above-described two-component agent according to the invention providing the time varying pH.

The invention also has the purpose of providing a composition and method for permanent shaping of hair, in which the pH decreases during the acting time, so that the reducing agent effectiveness is reduced during the acting time. The reduction in the pH during treatment is controlled or adjusted so that the hair structure is protected, while sufficient shaping of the hair is provided.

It has now been surprisingly found that the above-described disadvantages of the methods according to the state of the art may be avoided by a method for permanent shaping hair, in which embodiments of the above-described two-component agent according to the invention are used. The components (A) and (B) in these embodiments include ingredients suitable for the permanent shaping of hair.

In these methods the components (A) and (B) are mixed to form a ready-to-apply permanent shaping composition immediately prior to application. Advantageously the first component (A) contains a keratin-reducing agent and a base and has an initial pH value of 7.5 to 10, while the second component (B) contains an acid, or vice versa. Then the hair is held in the desired shape immediately before and/or after applying the ready-to-apply permanent shaping composition. Then the hair is rinsed after a predetermined acting time of the permanent shaping composition on the hair, oxidative after-treated, rinsed again with water, if necessary, put in a water wave and then dried. According the invention the permanent shaping composition has a time varying pH that varies over a time interval from 1 to 60 minutes. Also less than 3 g of the acid and/or base is soluble in water at 20° C. Preferably the acid is a hydrophobic acid, especially a dicarboxylic acid with 6 to 22 carbon atoms, such as sebacic acid, dodecanoic dicarboxylic acid and tetradecanoic dicarboxylic acid. The base can be an inorganic base, such as LiOH, NaOH, KOH, $Ca(OH)_2$, ammonia and hydrazine. The base can also be an organic base with 1 to 20 carbon atoms, such as an alkyl amine, alkyl diamine or an alkylol amine. The agent or product can also include from 1 to 20 percent by weight of lipophilic compound, such as a fatty alcohol, a triglyceride, a paraffin oil or a wax.

Preferably the initial pH of the alkaline permanent shaping composition is from 8 to 9.5 and drops from 0.8 to 2.0 pH units within 10 to 30 minutes. Especially preferably the initial pH value of the permanent shaping composition drops to a value from 6.5 to 7.3 within 7 to 20 minutes. The application temperature amounts preferably to 20 to 45° C., especially preferably from 30 to 40° C.

The decrease in alkalinity, the dissociation degree of the reducing agent and thus the waving effectiveness during the acting time can be controlled to the desired extent by suitable selection of acids and bases and their concentrations.

It is preferable when the initial pH value is reduced by at least one unit to a pH value between 6.5 and 7.3 within 7 to 20 minutes. When the two-component agent provides a permanent wave composition the initial pH is 8 to 9.5 and the pH is reduced from 0.8 to 2.0 units within 10 to 30 minutes.

In a similar preferred embodiment of the invention the two component-permanent wave agent is a hair curling agent, whose pH value is initially 11 to 13 and the pH is reduced by 2 to 4 units within 10 to 30 minutes.

The acting time of the permanent shaping composition may be shortened by heating during the hair shaping treatment.

The keratin-reducing agent used in the two-component permanent shaping composition may especially be thioglycolic acid, thioglycolic acid amide, thioglycerin, thiolactic acid, 3-mercaptopropionic acid, cysteine, cysteamine, homocysteine, alkyl or acyl cysteine or the salts of these compounds, especially ammonium thioglycolate. The keratin-reducing agent is contained in the ready-to-apply composition for permanent hair shaping in an amount of from 1 to 25 percent by weight, preferably from 5 to 15 percent by weight.

Understandably the ready-to-use composition for permanent shaping can contain all those known additive ingredients commonly employed in this type of composition. For example, these additive ingredients include thickening agents, such as bentonite, fatty acids, starch, polyacrylic acid and its derivatives, cellulose derivatives, alginate, petrolatum (Vaseline®), paraffin oils; wetting agents and emulsifiers from the classes of anionic, cationic, amphoteric or non-ionic surface-active agents, for example fatty alcohol sulfates, fatty alcohol ether sulfates, alkyl sulfonates, alkylbenzene sulfates, quaternary ammonium salts, alkylbetaines, ethoxylated alkyl phenols, fatty acid alkanol amies or ethoxylated fatty acid esters; further turbidity-inducing agents, such as polyethylene glycol esters; alcohols, such as ethylene glycol, 1,2-propandiol, 1,3-propandiol, 1,2-butandiol, 1,3-butandiol, 1,4-butandiol, 1,2-pentandiol, 1,3-pentandiol, 1,4-pentandiol, 1,5-pentandiol and glycerol; sugars, such as D-glucose; solvating agents, stabilizers, buffer substances, perfume oils, dyestuffs and hair conditioning and hair care ingredients, such as cationic polymers, lanolin derivatives, cholesterol, pantothenic acids and betaines.

The above-mentioned ingredients are used in amounts that are conventional for commercial preparations for permanent shaping of hair, e.g. the wetting agents and emulsifiers are employed in concentrations of 0.2 to 30 percent by weight, the alcohols in amounts of from 0.1 to 20 percent by weight, the turbidity inducing agents, perfume oils and dyestuffs in amounts of 0.01 to 1 percent by weight respectively, the buffer substances in an amount of from 0.1 to 10 percent by weight, the sugars, solvating agents, stabilizers and hair conditioning and hair care ingredients, in amounts of from 0.1 to 5 percent by weight respectively, while the thickeners and solvating agents, in amounts of from 0.5 to 20 percent by weight.

This permanent shaping agent according to the invention can also include from 1 to 30 percent by weight of a so-called swelling and penetration substances, such as dipropylene glycol monomethyl ether, 2-pyrrolidone or imidazolidin-2-one, to increase its effectiveness.

The ready-to-apply agent for permanent shaping of hair is obtained by mixing components (A) and (B). It is best when the ready-to-apply agent is made immediately (i.e. 2 seconds to 3 minutes) prior to application by mixing the two components. The component (B) preferably includes the keratin-reducing material and a base. The component (A) preferably includes the acid (or vice versa). One component can be present in solid form, when the other is present in liquid form. Both components are preferably liquid or thickened. The composition is packaged advantageously as a two-component agent or product.

In a preferred embodiment of the method according to the invention for permanent shaping of hair the hair is treated as follows: First the component (A) containing the acid is provided to or mixed with the component (B) containing the mercapto compound and the base in solution. Then the ready-to-apply shaping composition is applied to the curled hair in the usual manner. The original pH of the mixture of 7.5 to 10 drops during the acting time to 6.0 to 7.5. The acting time depends on the strength of the desired curling and on the treatment temperature.

After an acting time sufficient for permanent shaping of hair, which amounts to from 5 to 30 minutes (10 to 30 minutes without heating or 5 to 20 minutes with heating), depending on the hair condition, the shaping agent effectiveness and the application temperature, the hair is rinsed with water and subsequently oxidatively after-treated ("fixed"). The after-treating agent is used, according the hair abundance, preferably in an amount of from 80 to 100 g.

For oxidative after-treatments in the curled or uncurled state any arbitrary after-treatment agent suitable for this sort of treatment may be used. For example, oxidizing agents used for this sort of after-treatment include potassium bromate, sodium bromate, sodium perborate, urea peroxide and hydrogen peroxide. The concentration of the oxidizing agent depends on the application time (usually 5 to 15 minutes) and the different application temperatures. Normally the oxidizing agent is present in an aqueous after-treatment composition in a concentration of from 0.5 to 10 percent by weight. The after-treatment composition can understandably contain additive ingredients, such as wetting agents, care materials, such as cationically active polymers, weak acids, buffer substances or peroxide stabilizers, and in a form of an aqueous solution an emulsion and in thickened form on an aqueous basis, for example as a cream, gel or paste. These additive ingredients can be contained in the after-treatment composition in amounts of from 0.1 to 10 percent by weight.

Subsequently the curlers are removed. In case it is necessary, the uncurled hair can be further oxidatively after-treated. Then the hair is rinsed with water, put in a water wave as needed and subsequently dried.

The composition and/or method produces an elastic, permanent and uniform treatment from the hair roots to the hair tips, without allergic reactions or sensitizing reactions, while largely protecting the hair structure from damage.

When the composition according to the invention is a two-component hair care agent, preferably two cationic hair care components are prepared, which are intimately mixed immediately prior to application. The two cationic hair care components are an acid care component (S) contains a carboxylic acid in a fatty alcohol phase (in which the otherwise usual acidification is not employed since the pH is already between 3 to 4), and a basic care component (care B). Acids with higher melting points, such as sebacic acid or octanedioic acid, must be melted in glycerol or oil bath at about 120° C. The time dependent pH change or behavior can either be made observable by means of a pH meter and/or by means of an indicator dye.

BRIEF DESCRIPTION OF THE SOLE FIGURE

FIG. 1 is a graphical illustration of the observed dependence of pH on time for a mixture of equal volumes of the care component S and the care component B described above.

EXAMPLES

Example 1

Two component-Hair care agent with Color Change at End of recommended Acting Time

| Raw Material | Acidic Component A (Care Component S) | Basic Component B (Care Component B) |
|---|---|---|
| Sebacic Acid | 2.0 g | 0.7 g |
| Myristyl amine | — | 2.0 g |
| Bromthymol Blue (pH Indicator) | — | 0.2 g |
| Cetylstearyl alcohol (Lanette ® O) | 4.0 g | 4.0 g |
| Cetyltrimethyl ammonium chloride | 1.0 g | 1.0 g |
| Water | To 100 g | To 100 g |
| pH value | 3.0 | 9.5 |

Preparation:
Care component S (Component A): The fatty alcohol is melted together with the hydrophobic acid at 90° C. with stirring in a water bath, until a clear phase is produced. The water phase comprising cetyltrimethyl ammonium chloride and water is heated at 85° C. It is emulsified by stirring into the liquid fatty phase at 850° C. The resulting emulsion is cooled to room temperature with stirring in a cooled water bath.
Care Component B (Component B): The fatty alcohol is melted together with the hydrophobic acid, the fatty amine and the indicator dye at 90° C. with stirring in a water bath, until a clear phase is produced. The water phase comprising cetyltrimethyl ammonium chloride and water is heated to 85° C. It is emulsified by stirring into the liquid fatty phase at 85° C. The resulting emulsion is cooled to room temperature with stirring in a cooled water bath.

Use: Immediately prior to application equal volumes of care component S and care component B are intimately mixed with each other. At least one pre-mixing (e.g. as in striped toothpaste) may occur in the final marketed product, for the two-component packaging. The final complete mixing of the components is performed while working the product into the hair.

The initial pH of the mixture should be 7.8. The present two-component care agent is equipped so that the end color is reached after about 10 minutes when equal volumes of both components are applied to all positions or locations. Deviation of the mixture ratio to favor the acid component A or to favor the basic component B leads, in contrast, to acceleration or a delay of the color change.

The care composition formed after mixing has an intense blue color, which changes to a pale yellow color during a time interval of 8 to 12 minutes.

Example 2

Two component-permanent wave agent with Time Dependent pH decreasing during its Acting Time

| Raw Material | Acidic Component A | Basic Component B |
|---|---|---|
| Sebacic Acid | 1.0 g | — |
| Hexadecylamine | — | 1.0 g |
| Cetylstearyl alcohol (Lanette ® O) | 2.0 g | 2.0 g |
| Ethoxylated cetylstearyl Alcohol (25 EO) | 0.5 g | 0.5 g |
| Thioglycolic acid | 10.5 g | 10.5 g |
| Ammonia, 25% | 5.7 g | 10.6 g |
| Water | To 100 g | To 100 g |
| pH value | 3.5 | 9.1 |

Immediately prior to application both components A and B are mixed in a ratio 1:1 and subsequently the ready-to-apply permanent shaping composition is applied to the hair. The pH of the mixture obtained is 8.5, but the pH decreases to a final pH value of 7.0 during the acting time of 15 minutes.

Example 3

Two component-creamy hair dyeing agent for Dyeing hair copper red

| Raw Material | Acidic Component A | Basic Component B |
|---|---|---|
| Tetradecanoic diacid | 2.00 g | — |
| Ammonia | — | 2.00 g |
| Ethoxylated lauryl alcohol (3 EO) | 4.00 g | 4.00 g |
| $C_{16-}$ to $C_{18-}$ fatty alcohol | 8.00 g | 8.00 g |
| Complex former | — | 0.20 g |
| Sodium sulfite | — | 1.00 g |
| Perfume oil | 0.50 g | 0.50 g |
| p-aminophenol | — | 0.10 g |

-continued

Two component-creamy hair dyeing agent for Dyeing hair copper red

| Raw Material | Acidic Component A | Basic Component B |
| --- | --- | --- |
| p-toluylenediamine | — | 0.20 g |
| o-nitro-p-phenylenediamine | — | 0.10 g |
| p-nitro-o-aminophenol | — | 0.05 g |
| Resorcinol | — | 0.05 g |
| Hydrogen peroxide | 6.00 g | — |
| Water | To 100 g | To 100 g |
| pH value | about 3.0 | about 10.1 |

Immediately prior to application both components A and B are mixed and subsequently the ready-to-apply creamy hair coloring composition is applied to the hair. The pH for the mixture is initially 9.5 but drops gradually or continuously into the neutral range during the 12 minute acting time.

The disclosure in German Patent Application 101 46 350.2 of Sep. 20, 2001 is incorporated here by reference. This German Patent Application describes the invention described hereinabove and claimed in the claims appended hereinbelow and provides the basis for a claim of priority for the instant invention under 35 U.S.C. 119.

While the invention has been illustrated and described as embodied in a two-component agent with a time varying pH gradient and methods for treating hair, it is not intended to be limited to the details shown, since various modifications and changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and is set forth in the following appended claims.

We claim:

1. A two-component agent consisting of one component (A) and another component (B) separate from said one component, wherein said one component (A) contains at least one acid, said another component (B) contains at least one base, and less than 3 g of at least one of said at least one base and said at least one acid are soluble in 100 ml of water at 20° C.;
    whereby a pH of a mixture of the one component (A) with the another component (B) automatically continuously or gradually changes with time during a time interval of one minute to 60 minutes after mixing said components.

2. The agent as defined in claim 1, wherein from 0.01 to 0.5 g of at least one of the at least one acid and the at least one base are soluble in 100 ml of water at 20° C.

3. The agent as defined in claim 1, wherein said at least one acid is a hydrophobic acid and said at least one base is an inorganic base or an organic base containing 1 to 40 carbon atoms, and less than 3 g of said hydrophobic acid are soluble in 100 ml of water at 20° C.

4. The agent as defined in claim 3, wherein said hydrophobic acid is a dicarboxylic acid having 6 to 22 carbon atoms.

5. The agent as defined in claim 3, wherein said hydrophobic acid is a dicarboxylic acid having 8 to 16 carbon atoms.

6. The agent as defined in claim 3, wherein said hydrophobic acid is sebacic acid, dodecanoic dicarboxylic acid or tetradecanoic dicarboxylic acid.

7. The agent as defined in claim 1, wherein said at least one base is an inorganic base selected from the group consisting of LiOH, NaOH, KOH, Ca(OH)$_2$, ammonia and hydrazine.

8. The agent as defined in claim 1, wherein said at least one base is an organic base with one to twenty carbon atoms.

9. The agent as defined in claim 8, wherein said organic base is selected from the group consisting of alkyl amines and alkylol amines.

10. The agent as defined in claim 1, containing from 0.01 to 10 percent by weight, based on a total amount of a mixture of said components (A, B), of said at least one base and said at least one acid respectively.

11. The agent as defined in claim 1, wherein the mixture of the components (A, B) has a pH varying with time, wherein a final pH of the mixture is reached from an initial pH of the mixture during a time period of 2 to 100 minutes.

12. The agent as defined in claim 11, wherein said time period is from 4 to 30 minutes.

13. The agent as defined in claim 12, wherein said final pH is lower than said initial pH.

14. A two-component agent consisting of one component (A) and another component (B), wherein said one component (A) contains at least one acid, said another corn component (B) contains at least one base, and less than 3 g of at least one of said at least one base and said at least one acid are soluble in 100 ml of water at 20° C.;
    whereby a pH of a mixture of the one component (A) with the another component (B) automatically continuously or gradually changes with time during a time interval of one minute to 60 minutes after mixing said components;
    wherein at least one of said components contains a pH indicator that changes color when said pH changes through a certain pH range.

15. The agent as defined in claim 1, consisting of a cosmetic agent.

16. The agent as defined in claim 15, wherein said cosmetic agent is a hair care product or a permanent hair shaping product.

17. A two-component agent consisting of one component (A) and another component (B), wherein said one component (A) contains at least one acid, said another component (B) contains at least one base, and less than 3 g of at least one of said at least one base and said at least one acid are soluble in 100 ml of water at 20° C.;
    whereby a pH of a mixture of the one component (A) with the another component (B) automatically continuously or gradually changes with time during a time interval of one minute to 60 minutes after mixing said components;
    wherein at least one of said components contains from 1 to 20 percent by weight of a lipophilic compound.

18. The agent as defined in claim 17, wherein said lipophilic compound is a fatty alcohol, triglyceride, paraffin oil or wax.

19. A two-component agent consisting of a first water-containing emulsion (A) and a second water-containing emulsion (B) separate from said first aqueous emulsion, wherein said first water-containing emulsion (A) contains a hydrophobic dicarboxylic acid and at least one lipophilic ingredient and said second water-containing emulsion contains at least one base;

wherein less than 3 g of said hydrophobic acid are soluble in 100 ml of water at 20° C.;

whereby a pH of a mixture of said first water-containing emulsion (A) with said second water-containing emulsion (B) automatically continuously or gradually changes with time during a time interval of one minute to 60 minutes after mixing said components.

20. The two-component agent as defined in claim 19, wherein said first and second water-containing emulsions each comprise at least one additive ingredient selected from the group consisting of thickening agents, anionic surfactants, cationic surfactants, amphoteric surfactants, nonionic surfactants, turbidity-inducing agents, alcohols, sugars, solvating agents, stabilizers, buffer substances, perfume oils, dyestuffs cationic polymers, lanolin derivatives, cholesterol, pantothenic acids and betaines.

* * * * *